United States Patent [19]
Cavicchi

[11] Patent Number: 4,816,689
[45] Date of Patent: Mar. 28, 1989

[54] DEVICE SERVING TO GENERATE INFRARED RADIATION, EFFECTIVE ON CUTANEOUS AND ON DEEP-SEATED TISSUE OF THE HUMAN BODY

[76] Inventor: Umberto Cavicchi, Via Orlandi, 3, 40068 San Lazzaro di Savena (Bologna), Italy

[21] Appl. No.: 47,191

[22] Filed: May 6, 1987

[30] Foreign Application Priority Data

May 13, 1986 [IT] Italy ................................. 3416 A/86

[51] Int. Cl.$^4$ .............................................. G21G 4/00
[52] U.S. Cl. ............................... 250/493.1; 250/495.1; 250/504 R
[58] Field of Search ............... 250/493.1, 495.1, 503.1, 250/504 R, 504 H; 362/293, 296, 310, 351

[56] References Cited

U.S. PATENT DOCUMENTS

| | | |
|---|---|---|
| 861,019 | 7/1907 | Coger ............................... 250/495.1 |
| 1,681,654 | 8/1928 | Asleson . | |
| 1,768,519 | 6/1930 | MacLagan . | |
| 2,275,745 | 3/1942 | Eastman . | |
| 2,469,412 | 3/1945 | Roebken ........................ 250/504 R |
| 2,660,925 | 12/1953 | Turner ................................. 362/296 |
| 2,852,980 | 9/1958 | Schroder ............................ 362/293 |
| 3,735,137 | 5/1973 | Bly .................................. 250/495.1 |
| 4,082,949 | 4/1978 | Bigelow .......................... 250/504 R |
| 4,672,211 | 6/1987 | Bartell ............................. 250/493.1 |

FOREIGN PATENT DOCUMENTS

883868 12/1961 United Kingdom .

Primary Examiner—Bruce C. Anderson
Attorney, Agent, or Firm—Fay, Sharpe, Beall, Fagan, Minnich & McKee

[57] ABSTRACT

The device disclosed comprises a light source located internally of a shield, and a photothermal converter embodied as a foil; light radiated from the source is exploited as energy, falling incident upon the converter in such a way that the radiation re-emitted is exclusively infrared and within the 8 ... 9 μm wavelength band, and capable of producing a marked therapeutic action both at cutaneous level and on deep-seated bone and internal body tissue.

10 Claims, 1 Drawing Sheet

DEVICE SERVING TO GENERATE INFRARED RADIATION, EFFECTIVE ON CUTANEOUS AND ON DEEP-SEATED TISSUE OF THE HUMAN BODY

BACKGROUND OF THE INVENTION

The invention disclosed relates to a device for generating therapeutic infrared radiation, effective both on cutaneous tissue and on deeper-seated tissue of the human body.

Conventionally, use is made in medicine of infrared rays having a wavelength of between 1 and 2μm. Such infrared rays are emitted by lamps sold on the open market, which are fitted either with a tungsten filament capable of temperatures between 2500° and 3000° C., or with electric resistances. Lamps of this conventional type are positioned at 50...60cm from the surface of the part of the human body to be treated, and the therapeutic effect is obtained by inducing thermogenesis in the affected area.

The essential shortcoming of near-region radiation generated by conventional infrared lamps consists in the fact that the therapeutic effect is limited, and restricted almost exclusively to the treatment of arthritic and osteoarthritic conditions (for which a low percentage of cures is obtained).

The object of the invention disclosed is to overcome the drawback thus outlined by providing a device capable of emitting infrared rays of wavelength and intensity such as prove highly effective from the therapeutic standpoint.

A further object of the invention is to permit of using infrared radiation in the field of cosmetic treatment (cellulitis, dermatitis &c.).

SUMMARY OF THE INVENTION

The stated objects, and others besides, are realized with a device according to the invention. Such a device comprises at least one light source (preferably an ordinary lamp) the light radiated from which is incident upon a photothermal converter which exhibits one dark, light-absorbent surface acting as a black body and directed toward the light source, and a surface opposite to the dark surface, by which radiation of exclusively infrared frequency is emitted.

The problem confronting the inventor is, how to combine a light source and photothermal converter in such a way as the enhance infrared radiation and permit of its exact regulation to more advantageous wavelengths (8 ... 9μm); this the invention succeeds in doing, and in a novel and effective manner.

In contrast to what is discernable from medical literature, which states generally that the infrared rays possessing greatest penetration fall within the near region (1 ... 1.5μm), though different authors are by no means all of one voice, it has been found with the device disclosed that wavelengths of the intermediate order mentioned above are in fact the more effective.

Contributing significantly to such effectiveness, moreover, is the intensity of the infrared emission obtained with a photothermal conversion medium. Practical evidence of this assertion is likewise available, inasmuch as the device disclosed has produced optimum results in therapy not only on commonplace arthritic and osteoarthritic conditions, but also on deeper seated organs such as the bronchi and the colon.

Accordingly, an essential advantage provided by the invention is that it produces a healing action not only on conditions already known to respond to infrared therapy, but also on those falling within the scope of internal pathology.

A further advantage of the invention may be discerned in the high percentages of cures effected, and of positive and lasting results obtained. In the great number of pathological conditions treated, 85 ... 90% success was obtained, and this without any additional use of drugs. Only in cases of osteoporosis does it become advisable to administer calcium or calcitonin for the purposes of correcting natural deficiency.

The applications mentioned below are medical, though application in other pathological fields are by no means ruled out.

Treatment effected with the device disclosed:
orthopaedic
subacute and chronic instances of osteoarthritis, arthritis, post-traumatic conditions;
percentage of complete cures or positive and lasting results: 80 ... 90%
internal
respiratory: chronic bronchitis, asthma, rhinitis, otitis;
digestive: colitis with marked constipation, posthepatitic conditions;
circulation: thrombo-angitis obliterans, lower limb disorders, nervous headache;
percentage of positive and lasting results likewise 80 ... 90%
dermatological
psoriasis, mycotic dermatitis, healing of scars: good results;
leucodermia (vitiligo) of relatively short history: appreciable results;
lipomatosis: reduction of approx 50% in volume of accumulated fat;
finally, it has been found that subjects treated for cervical osteoarthritis and suffering concurrently from anxiety or depression, have gained a lasting restabilization of their nervous system.

Another advantage of the device disclosed is that of its extreme simplicity in construction, considered in the light of the results obtainable.

Lastly, it will be noted that the device features significantly low consumption of electrical power.

BRIEF DESCRIPTION OF THE DRAWINGS

The invention will now be described in detail, by way of example, with the aid of the accompanying drawings, in which.

DESCRIPTION OF THE PREFERRED EMBODIMENTS

Figure 1:
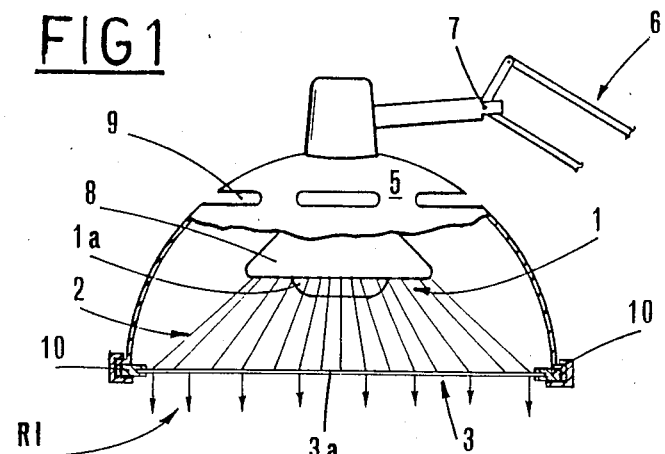
FIG. 1 is a schematic representation of the device disclosed, with certain parts omitted better to reveal others.
Figure 2:
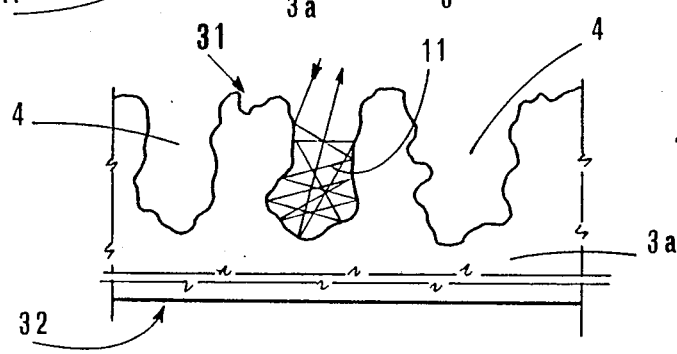
FIG. 2 is an illustration of the photothermal foil converter according to the invention, as seen under the microscope.

With reference to the drawings, a preferred embodiment of the device disclosed comprises a light source 1, which in the example illustrated is an ordinary electric lamp 1a, the light 2 radiated from which is incident upon a photothermal converter 3 providing the actual surface from which infrared radiation is emitted.

In the drawings, the photothermal converter 3 is embodied as a foil 3a of highly conductive metal, copper, for example, or copper and nickel &c. Use has in fact been made of a material already known for its photothermal conversion properties, though employed hitherto chiefly in solar heating panels, namely "Coppersun".

Foil 3a of the type mentioned has an absorbent surface 31 on one side, treated in such a way as to exhibit a myriad of microscopic cavities 4. A ray of light thrown by the lamp 1a produces a considerable number of reflections 11, dissipating its energy in so doing; such energy converts to heat, and is then transformed into infrared radiation RI emitted from the remaining surface 32 of the foil 3a, which is rendered highly emissive and reflective (it will be noted that the radiation emitted is exclusively infrared).

Power output from the lamp will be proportioned such that the foil 3a can emit infrared radiation RI at a wavelength of approx 8 ... 9μm. To obtain such intermediate wavelengths, the foil 3a must be held at a temperature of 80°... 90° C.

More exactly, the electric lamp is accommodated internally of an opaque shield 5 carried by an arm 6 to which it is pivotably attached via a hinge 7. In a preferred embodiment, the electric lamp 1a will be surrounded by a baffle 8 so as to concentrate the light down onto the foil 3a beneath and permit of creating slots 9 in the shield that vent the hot air upwards without any dispersion of the light source. The foil 3a is attached to the shield 5 by way of a rigid peripheral edging 10 made fast to the foil itself and suitably retained in position.

Figure 3:
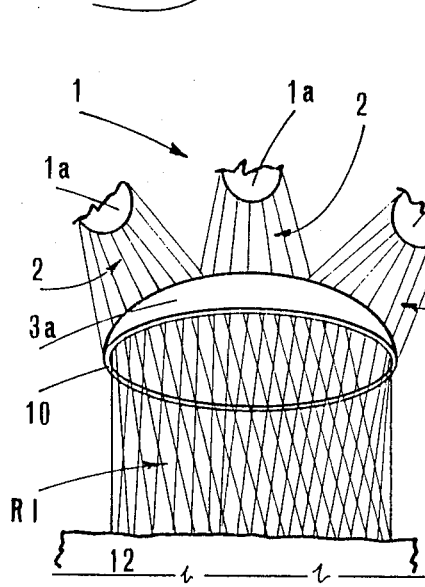
FIGS. 3 and 4 show two examples of the shape of a foil converter as in FIG. 2.
Figure 4:
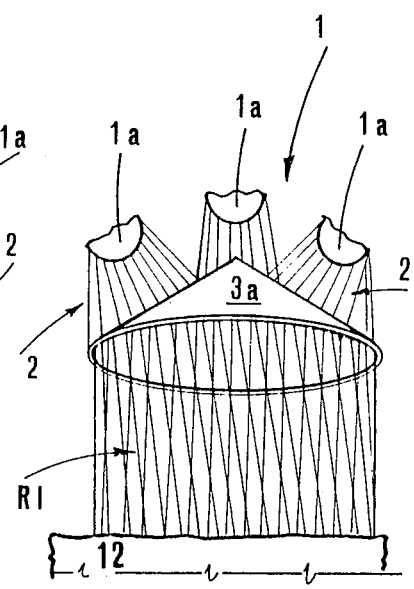

In a simple embodiment, the foil 3a will be flat, as illustrated in FIG. 1. However, the option exists of more advantageous geometry, say, a cone (FIG. 4), or a dome (FIG. 3), or any other shape with downwardly divergent walls; thus, the infrared rays RI can be gathered into a vertical beam concentrated at the tissue 12 to be treated.

The additional option exists of embodying both the shield 5 and the foil 3a in a shape to match the somatic profile of the surface treated, entirely or in part.

Clearly enough, numerous variations might be made to the basic design of the device, in terms of construction, of technical features and of practical application, without straying from the essential concept. For instance, other materials might be used for photothermal conversion, as long as the surface of one side is capable of absorbing light, and that of the opposite side is emissive.

It will also be clear that the emitting surface of the device disclosed is generously proportioned, and accordingly, a greater number of infrared rays can be generated per unit surface area of the treatment zone than is the case with significantly limited emitting surface areas such as those of a filament or a resistance lamp.

Finally, it will be observed that the device disclosed is abundantly simple in construction, and features a low electrical power supply requirement amongst its other advantages.

What is claimed is:

1. A device serving to generate infrared radiation for therapeutic purposes, effective on cutaneous and deep-seated tissue of the human body, comprising:
   a light source;
   a photothermal converter comprising a foil of highly conductive metal upon which light radiated from the source falls incident, said foil being provided on one side with a light-absorbent surface directed toward the light source and comprising a myriad of microscopic cavities internally of which each light ray from the source is reflected many times over so that its entire energy content is converted gradually within the foil, and wherein an opposite side of said foil is provided with a surface which emits radiation of exclusively infrared frequency.

2. A device as in claim 1, wherein the light-absorbent surface of the foil is dark in appearance, and functions as a black body.

3. A device as in claim 1, wherein the light source is an electric lamp, the power output from said lamp being proportioned such that the emissive surface of the foil is raised to a temperature of $T \leq 89°$ C. for a corresponding emitted infrared radiation wavelength of $n \geq 8\mu m$.

4. A device as in claim 3, wherein the light source comprises an ordinary electric lamp and wherein the device further comprises:
   an opaque shield in which said lamp is accommodated;
   an arm for carrying the opaque shield; and,
   a hinge located between the shield and the arm for pivotably attaching the arm to the shield, and wherein the foil comprises a rigid peripheral edging insertable into and removable from the opaque shield.

5. A device as in claim 4, wherein the foil is flat.

6. A device as in claim 4, wherein the foil is a cone.

7. A device as in claim 4, wherein the foil is a dome.

8. A device as in claim 4, further comprising:
   a baffle fitted between the electric lamp and the shield, and
   vent slots fashioned in the shield above the level of the baffle.

9. A device as in claim 1 wherein said foil surface which emits radiation is highly reflective.

10. A method for treating a human body with infrared radiation for therapeutic purposes, comprising:
    providing a light source and a photothermal converter comprising a foil of highly conductive metal comprising a myriad of microscopic cavities on which light is to be radiated by the light source;
    shaping the foil to match a somatic profile of a body surface to be treated;
    interposing the foil between the light source and the body surface to be treated;
    radiating light from the light source onto a first surface of the foil; and,
    emitting converted infrared radiation from a second surface of the foil onto the body surface to be treated.

* * * * *